(12) United States Patent
Litvin

(10) Patent No.: US 11,213,382 B2
(45) Date of Patent: Jan. 4, 2022

(54) KERATOPROSTHESIS AND USES THEREOF

(71) Applicant: CORNEAT VISION LTD., Ra'anana (IL)

(72) Inventor: Gilad Litvin, Moshav Sde Varburg (IL)

(73) Assignee: CORNEAT VISION LTD, Ra'anana (IL)

(*) Notice: Subject to any disclaimer, the term of this patent is extended or adjusted under 35 U.S.C. 154(b) by 45 days.

(21) Appl. No.: 16/858,767

(22) Filed: Apr. 27, 2020

(65) Prior Publication Data

US 2020/0253718 A1    Aug. 13, 2020

Related U.S. Application Data

(62) Division of application No. 15/580,339, filed as application No. PCT/IL2016/050597 on Jun. 8, 2016, now Pat. No. 10,667,902.

(60) Provisional application No. 62/172,588, filed on Jun. 8, 2015.

(51) Int. Cl.
*A61F 2/14* (2006.01)
*A61F 9/007* (2006.01)
*A61F 9/013* (2006.01)

(52) U.S. Cl.
CPC ............ *A61F 2/142* (2013.01); *A61F 9/007* (2013.01); *A61F 9/00781* (2013.01); *A61F 2/1451* (2015.04); *A61F 2/1453* (2015.04); *A61F 9/013* (2013.01); *A61F 9/0133* (2013.01)

(58) Field of Classification Search
CPC ....... A61F 2/142; A61F 2/1451; A61F 2/1453
See application file for complete search history.

(56) References Cited

U.S. PATENT DOCUMENTS

| | | |
|---|---|---|
| 3,737,508 A | 6/1973 | Weir et al. |
| 3,950,478 A | 4/1976 | Kenworthy et al. |
| 3,996,321 A | 12/1976 | Weinberger |
| 4,189,336 A | 2/1980 | Hutflesz |
| 4,402,900 A | 9/1983 | Berry, Jr. |
| 4,421,707 A | 12/1983 | Kourtz et al. |
| 4,431,602 A | 2/1984 | Behrens et al. |
| 4,557,732 A | 12/1985 | Hahnke et al. |
| 4,643,657 A | 2/1987 | Achelpohl et al. |
| 4,804,511 A | 2/1989 | Pieper et al. |
| 5,002,474 A | 3/1991 | Hoekstra |
| 5,122,329 A | 6/1992 | Mort et al. |
| 5,282,851 A | 2/1994 | Jacob-Labarre |
| 5,387,387 A | 2/1995 | James et al. |
| 5,667,743 A | 9/1997 | Tai et al. |
| 6,106,552 A | 8/2000 | Lacombe et al. |

(Continued)

FOREIGN PATENT DOCUMENTS

| | | |
|---|---|---|
| AU | 22627602 | 11/2002 |
| CN | 1266669 A | 9/2000 |

(Continued)

OTHER PUBLICATIONS

Jia-Jia et al. "Advancement of keratoprosthesis research" International Journal of Ophthalmology 2008, Sec. 2.5 p. 563; Abstract.

*Primary Examiner* — Javier G Blanco
(74) *Attorney, Agent, or Firm* — Mark S. Cohen; Pearl Cohen Zedek Latzer Baratz LLP

(57) ABSTRACT

The present invention provides a keratoprosthesis assembly comprising a central optical core; and a peripheral skirt comprising at least one porous biocompatible layer and methods of using it in keratoprosthesis procedures.

6 Claims, 6 Drawing Sheets

(56) References Cited

U.S. PATENT DOCUMENTS 6,248,273 B1 6/2001 Benin et al.
6,252,031 B1 6/2001 Tsutsumi et al.

FOREIGN PATENT DOCUMENTS

| CN | 102283720 A | 12/2000 |
|---|---|---|
| EP | 0446197 | 9/1991 |
| RU | 2367379 C1 | 9/2009 |
| WO | WO 2002/43622 | 6/2002 |
| WO | WO 2002/049535 | 6/2002 |
| WO | WO 2002/049536 | 6/2002 |
| WO | WO 2002/049678 | 6/2002 |
| WO | WO 2002/074189 | 9/2002 |
| WO | WO 2002/074190 | 9/2002 |
| WO | WO 2002/074191 | 9/2002 |
| WO | WO 2002/089709 | 11/2002 |
| WO | WO 2005/032400 | 4/2005 |
| WO | WO 2005/065578 | 7/2005 |
| WO | WO 2008/127653 | 10/2008 |
| WO | WO 2009/135068 | 11/2009 |

KERATOPROSTHESIS AND USES THEREOF

CROSS-REFERENCE TO RELATED APPLICATION

This application is a divisional application of U.S. patent application Ser. No. 15/580,339, filed Jun. 8, 2016, which is hereby incorporated by reference.

TECHNOLOGICAL FIELD

The present invention relates to keratoprosthesis assemblies (artificial cornea) and methods of using them.

BACKGROUND

Diseases affecting the cornea are a major cause of blindness worldwide, second only to cataract in overall importance. According to the World Health Organization, approximately 2 million new cases are reported each year. Over 50 million people in the world are blind in one or both eyes from corneal injury or disease. Degradation of visual acuity impacts many more.

For various reasons, current solutions for corneal blindness and diseases only address 5%-10% of cases. To date, most patients are treated with Keratoplasty—a procedure that relies on transplanting corneal tissue harvested from the deceased. All artificial cornea solutions that are based on implants have failed to address this potential for diversified reasons. Due to risks, complexity, and costs, these are selectively used as a last resort for patients that are not suited for corneal transplant or have failed one. Current solutions for corneal blindness are divided to Keratoplasty (Corneal transplantation) and Keratoprosthesis (Artificial cornea).

During keratoplasty surgery the graft is taken from a recently deceased donor with no known diseases or other factors that may affect the chance of survival of the donated tissue or the health of the recipient. The disadvantage of keratoplasty is a lack of donor tissue, the complexity and costs of operating a cornea bank, and the limited applicability to only some cases. For example, corneal diseases and injuries that leads to vascularization (penetration of blood vessels into the corneal tissue) are not suitable for keratoplasty. Multiple grafting also leads to elevated risk for rejection/failure.

When using an artificial cornea the procedure is known as keratoprosthesis. Traditionally, keratoprosthesis is recommended after a patient has had a failure of one or more donor corneal transplants. While different types of Keratoprosthesis have been approved for limited use by the FDA (see Salvador-Culla et al. *Journal of Functional Biomaterial.* 2016, 7, 13, with a review of recent advances in the field of keratoprosthesis), the only viable solution in the marketplace today is the Boston KPro. Boston KPro is approved by the FDA only for cases that cannot be addressed by Keratoplasty. This is due to many complications and the need for close and lifelong monitoring by an ophthalmologist familiar with the Boston KPro. Life-long topical steroids such as prednisolone acetate is necessary in all KPro eyes to prevent inflammation.

There are multiple disadvantages and failures associated with the known keratoprosthesis options, including diversified postoperative complications which are mainly a result of the device intervention in the physiology of the anterior chamber. Most of the patients (60%-75%) develop glaucoma, elevated intraocular pressure, which can lead to blindness, limited field of vision and cataract. Furthermore, there is poor biointegration of the known keratoprosthesis that necessitates daily antibiotic drops, lifelong treatment with topical steroids, and intensive lifelong ophthalmologist follow up.

After the implantation of known keratoprosthesis the access to the internal parts of the eye for performing surgical procedures such as cataract and retinal surgery is very limited at best. Due to this, the primary keratoprosthesis surgery is often combined with other procedures including implantation of glaucoma filtration devices, and a cataract surgery (replacing the lens with synthetic Intra Ocular Lens) making the procedure longer, more dangerous and costly.

GENERAL DESCRIPTION

The present invention aims at improving the optical quality of the artificial graft, better bio-integration and improved resistance to trauma.

Thus, the present invention provides a keratoprosthesis comprising: (a) a central optical core; and (b) a peripheral skirt (located around and substantially surrounding said optical core) comprising at least one porous biocompatible layer having pore size of at least about 2 µm.

The term "keratoprosthesis" should be understood to encompass an artificial cornea used in the keratoprothesis procedure when replacing a diseased cornea of a subject in need thereof. The terms "keratoprosthesis assembly", "artificial cornea" and "artificial cornea assembly" are used herein interchangeably. Thus, the artificial cornea of the invention comprises a central optical core which is used to cover the anterior chamber of the eye, located at the center of the artificial cornea of the invention and a peripheral skirt located around said optical core traversing the anterior sclera beneath the conjunctiva-tenon complex.

The term "central optical core" of an artificial cornea of the invention (keratoprosthesis of the invention) provides the center part of the assembly which functions as the optical part of the keratoprosthesis covering the anterior chamber of the eye (after trephination of the diseases cornea). The optical core can be flexible in some embodiments, and can be rigid in others. The optical core is made from an acrylic, clear polymer, with varying dioptric power in accordance with the need of the subject.

In some embodiments, said central optical core comprises acrylic, silicate or other clear, durable polymer and any combinations thereof.

The optical core optionally further comprises an external layer repelling optical depositions. This external layer might be made of a silicone hydrogel similar to contact lenses.

In some embodiments, said optical core further comprises an extrusion centrally and posteriorly allowing for placement into a trephined cornea so to traverse the width of the recipient cornea.

In some embodiments, said central core extends towards the anterior chamber of the eye. Under these embodiments, the central core comprises edges extending below the surface formed by the central core and skirt of the assembly of the invention that allow it to extend into the anterior chamber of the eye. Thus, said central core further comprises an extended part (that is made of the same or other material) which extends on the concaved side of the assembly (towards the conjunctiva of the eye, when placed on the eye of a subject upon keratoprosthesis procedure). The extended part can have the same or different (in some embodiments smaller and in other embodiments larger) circumvent as that of the central transparent core. In other embodiments, said peripheral skirt is extended towards the conjunctiva of the eye.

The extended portion of the central core forms at least one groove extending from the posterior surface of the core that enables it to snap into the trephinted cut of the cornea. In some embodiments, the central optical core further comprises at least one extended groove having a width of at least about 0.25 mm (in other embodiments about 0.25 mm to about 1 mm).

In some embodiments, said central optical core has a diameter ranging from about 3 to about 15 mm. In other embodiments, said central optical core has a diameter of at least 3 mm. In other embodiments, said central optical core has a diameter in the range of about 3 to about 6 mm. In further embodiments, said central optical core has a diameter in the range of between 6 to 14 mm.

In further embodiments, said central optical core has a thickness ranging from about 500 micrometers to 3000 micrometers. In other embodiments said central optical core has a thickness ranging from about 500 micrometers to 2500 micrometers. In further embodiments said central optical core has a thickness ranging from about 500 micrometers to 1500 micrometers.

In other embodiments, said central optical core has a diopter ranging from about 10 to about 70 diopters.

In other embodiments, said central optical core further comprises at its rim (i.e. the margin that is in contact with the skirt) at least one hole or open arc.

The term "peripheral skirt" should be understood to encompass the part of the keratoprosthesis of the invention that surrounds substantially all the perimeter of the central optical core of the assembly. Said skirt comprises at least one porous biocompatible layer as defined herein above and below.

In some embodiments, said peripheral skirt is extended towards the conjunctiva of the eye. In further embodiments, said peripheral skirt is formed in a manner that enables placing it under the conjunctiva of the eye. Placing of the skirt beneath the conjunctiva is performed after dissecting the conjunctiva from its limbal anchorage (this procedure is termed peritomy) and elevating it so to create a space to accommodate the said skirt.

In some embodiments, said peripheral skirt has a width of at least 3 mm. In other embodiments, said peripheral skirt has a width of between 3 mm to 9 mm. In further embodiments, said peripheral skirt has a width ranging from about 4 to about 6 mm.

In some embodiments, said peripheral skirt has a thickness ranging from about 100 to about 2000 micron.

In some embodiments, said peripheral skirt further comprises a biomolecule or an antibiotic agent. In other embodiments, said biomolecule is selected from a protein, type I collagen, fibronectin, or TGF-beta 2, heparin, growth factors, antibodies, antimetabolites, chemotherapeutic agents, and any combinations thereof. In further embodiments, said biomolecule or antibiotic is covalently attached to said at least one porous biocompatible layer.

The term "porous biocompatible layer" should be understood to encompass any type of layer (or film) formed from material that has the ability to perform its desired function with respect to a medical therapy (i.e. keratoprosthesis), without eliciting any undesirable local or systemic effects in the recipient or beneficiary of that therapy, but generating the most appropriate beneficial cellular or tissue response in that specific situation, and optimizing the clinically relevant performance of that therapy. The biocompatible layer of the skirt of the assembly of the invention allows the implanted artificial cornea to exist in harmony with tissue it is in contact with without causing deleterious changes. The layer is porous, having pore size of at least at least about 2 μm (when referring to pore size it should be understood to relate to the average pore sizes).

In some embodiments, said porous biocompatible layer is a fibrous porous biocompatible layer (i.e. the layer or film is formed of fibers), having pore size of at least about 2 μm.

In some embodiments, at least one porous biocompatible layer has pores of between about 2 μm to about 100 μm in width.

In other embodiments, said at least one porous biocompatible layer is a polymeric layer. Thus, under this embodiment, the layer or film of the skirt is made of at least one polymer material.

In other embodiments, said at least one porous biocompatible layer is a nonwoven fabric. Thus, under this embodiment, said layer or film of the skirt is a fabric-like material made from long fibers, bonded together by chemical, mechanical, heat or solvent treatment.

In further embodiments, said porous biocompatible layer comprises nanofibers. Thus, under this embodiment, the skirt is formed of fibers with diameters of less than 2000 nanometres. In some embodiments, nanofibers are produced by any type of process including, but not limited to melt processing, interfacial polymerization, electrospinning, anti-solvent-induced polymer precipitation, electrostatic spinning, catalytic synthesis and any combinations thereof.

In further embodiments, said at least one porous biocompatible layer comprises poly(DTE carbonate) polycaprolactone (PCL), polylactic acid (PLA), poly-L-lactic acid (PLLA), Poly(DL-lactide-co-caprolactone, Poly(ethylene-co-vinyl acetate) vinyl acetate, Poly(methyl methacrylate), Poly(propylene carbonate), Poly(vinylidene fluoride), Polyacrylonitrile, Polycaprolactone, Polycarbomethylsilane, Polylactic acid, Polystyrene, Polyvinylpyrrolidone, poly vinyl alcohol (PVA), polyethylene oxide (PEO), polyurethane, polyvinyl chloride (PVC), hyaluronic acid (HA), chitosan, alginate, polyhydroxybuyrate and its copolymers, Nylon 11, Cellulose acetate, hydroxyappetite, poly(3-hydroxybutyric acid-co-3-hydroxyvaleric acid), poly(DL-lactide), polycaprolactone, and poly(L-lactide) or any combination thereof.

In some further embodiments, said porous biocompatible layer comprises electrospun nanofibers. In another embodiment, said at least one porous biocompatible layer is formed by electrospinning process.

The term "electrospinning" or "electrospun" or any of its lingual deviations should be understood to encompass a process using an electrical charge to draw very fine (typically on the micro or nano scale) fibers from a liquid. Electrospinning from molten precursors is also practiced; this method ensures that no solvent can be carried over into the final product. The fibers produced using electrospinning processes have increased surface area to volume ratio. Various factors are known to affect electrospun fibers include, but are not limited to: solution viscosity, surface tension, electric field intensity and distance.

In a typical electrospinning process a sufficiently high voltage is applied to a liquid droplet of a polymeric material (a polymer solution, a monomeric precursor thereof, sol-gel precursor, particulate suspension or melt), the body of the liquid becomes charged, and electrostatic repulsion counteracts the surface tension and droplet is stretched, at a critical point a stream of liquid erupts from the surface. If the molecular cohesion of the liquid is sufficiently high, stream breakup does not occur (if it does, droplets are electrosprayed) and a charged liquid jet is formed. As the jet dries in flight, the mode of current flow changes from ohmic to convective as the charge migrates to the surface of the fiber. The jet is then elongated by a whipping process caused by electrostatic repulsion initiated at small bends in the fiber, until it is finally deposited on the grounded collector. The elongation and thinning of the fiber that results from this bending instability leads to the formation of uniform fibers with nanometer-scale diameters.

Biocompatible polymers which may be applied in an electrospinning process include but are not limited to poly (DTE carbonate) polycaprolactone (PCL), polylactic acid (PLA), poly-L-lactic acid (PLLA), Poly(DL-lactide-co-caprolactone, Poly(ethylene-co-vinyl acetate) vinyl acetate, Poly(methyl methacrylate), Poly(propylene carbonate), Poly(vinylidene fluoride), Polyacrylonitrile, Polycaprolactone, Polycarbomethylsilane, Polylactic acid, Polystyrene, Polyvinylpyrrolidone, poly vinyl alcohol (PVA), polyethylene oxide (PEO), polyvinyl chloride (PVC), hyaluronic acid (HA), chitosan, alginate, polyhydroxybuyrate and its copolymers, Nylon 11, Cellulose acetate, hydroxyappetite, or any combination thereof. Biodegradable and biocompatible polymers include but are not limited to poly(3-hydroxybutyric acid-co-3-hydroxyvaleric acid), poly(DL-lactide), poly urethane, polycaprolactone, and poly(L-lactide) or any combination thereof.

Electrospun fibers are typically several orders in magnitude smaller than those produced using conventional spinning techniques. By optimizing parameters such as: i) the intrinsic properties of the solution including the polarity and surface tension of the solvent, the molecular weight and conformation of the polymer chain, and the viscosity, elasticity, and electrical conductivity of the solution; and ii) the operational conditions such as the strength of electric field, the distance between spinneret and collector, and the feeding rate of the solution, electrospinning is capable of generating fibers as thin as tens of nanometers in diameter. Additional parameters that affect the properties of electrospun fiber include the molecular weight, molecular-weight distribution and structure (branched, linear etc.) of the polymer, solution properties (viscosity, conductivity and surface tension), electric potential, flow rate and concentration, distance between the capillary and collection screen, ambient parameters (temperature, humidity and air velocity in the chamber), motion of target screen (collector) and so forth. Fabrication of highly porous fibers may be achieved by electrospinning the jet directly into a cryogenic liquid. Well-defined pores developed on the surface of each fiber as a result of temperature-induced phase separation between the polymer and the solvent and the evaporation of solvent under a freeze-drying condition.

Several approaches have been developed to organize electrospun fibers into aligned arrays. For example, electrospun fibers can be aligned into a uniaxial array by replacing the single-piece collector with a pair of conductive substrates separated by a void gap. In this case, the nanofibers tend to be stretched across the gap oriented perpendicular to the edges of the electrodes. It was also shown that the paired electrodes could be patterned on an insulating substrate such as quartz or polystyrene so the uniaxially aligned fibers could be stacked layer-by-layer into a 3D lattice. By controlling the electrode pattern and/or the sequence for applying high voltage, it is also possible to generate more complex architectures consisting of well-aligned nanofibers.

Electrospun nanofibers could also be directly deposited on various objects to obtain nanofiber-based constructs with well-defined and controllable shapes. In addition, one can manually process membranes of aligned or randomly oriented nanofibers into various types of constructs after electrospinning: for example, fabrication of a tube by rolling up a fibrous membrane or the preparation of discs with controllable diameters by punching a fibrous membrane.

The present invention relates to any eletrospinning technique known in the art, which includes *Electrospinning*, J. Stanger, N. Tucker, and M. Staiger, I-Smithers Rapra publishing (UK), *An Introduction to Electrospinning and Nanofibers*, S. Ramakrishna, K. Fujihara, W-E Teo, World Scientific Publishing Co. Pte Ltd (June 2005), *Electrospinning of micro- and nanofibers: fundamentals and applications in separation and filtration processes*, Y. Fillatov, A. Budyka, and V. Kirichenko (Trans. D. Letterman), Begell House Inc., New York, USA, 2007, which are all incorporated herein by reference in their entirety.

Suitable electrospinning techniques are disclosed, e.g., in International Patent Application, Publication Nos. WO 2002/049535, WO 2002/049536, WO 2002/049536, WO 2002/049678, WO 2002/074189, WO 2002/074190, WO 2002/074191, WO 2005/032400 and WO 2005/065578, the contents of which are hereby incorporated by reference. It is to be understood that although the according to the presently preferred embodiment of the invention is described with a particular emphasis to the electrospinning technique, it is not intended to limit the scope of the invention to the electrospinning technique. Representative examples of other spinning techniques suitable for the present embodiments include, without limitation, a wet spinning technique, a dry spinning technique, a gel spinning technique, a dispersion spinning technique, a reaction spinning technique or a tack spinning technique. Such and other spinning techniques are known in the art and disclosed, e.g., in U.S. Pat. Nos. 3,737,508, 3,950,478, 3,996,321, 4,189,336, 4,402,900, 4,421,707, 4,431,602, 4,557,732, 4,643,657, 4,804,511, 5,002,474, 5,122,329, 5,387,387, 5,667,743, 6,248,273 and 6,252,031 the contents of which are hereby incorporated by reference.

In some embodiments, said optical core and peripheral skirt are mechanically attached to each other (using for example mechanical means for attaching the core to the skirt, such as for example a strip of layer connecting them or a suture). In other embodiments, said optical core and peripheral skirt are chemically attached to each other (using for example any gluing or connecting component, fusing them together using heat or pressure and so forth).

In a further aspect the invention provides a procedure for implanting a keratoprosthesis in a subject in need thereof comprising the steps of:

Providing a keratoprosthesis according to the invention;
Performing a 360 degree peritomy in the eye of said subject;
Elevating and dissecting both tenon capsule and conjunctiva from sclera of the eye of said subject;
Performing trephination of central cornea of said subject;
Placing the transparent central core of said keratoprosthesis into the trephined space of said subject cornea;
Placing the peripheral skirt of said keratoprosthesis under the dissected tenon capsule and conjunctiva of said subject;
Optionally suturing skirt to sclera, or placing the skirt on bare sclera without anchoring it to the tissue;
Replacing tenon capsule and conjunctiva onto the skirt of the keratoprosthesis; and
Optionally suturing and repositioning conjunctiva to original configuration.

The procedure of implanting the keratoprosthesis assembly of the invention is thus a single staged procedure. The eye is filled with viscoelastic material. A peritomy of 360 degrees is made elevating both conjunctiva and tenon. Trephination of the central cornea is carried out. The optical zone is inserted into the trephined space. The bio-integrating skirt is laid on the bare sclera and optionally sutured to it. The tenon and conjunctiva are put back in place over the porous skirt and sutured tight. Viscoelastic is replaced with BSS (balanced saline solution).

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 4A shows an exemplary central optical core part of the keratoprosthesis and FIG. 4B shows an exemplary central optical core with the peripheral skirt.

DETAILED DESCRIPTION OF EMBODIMENTS

Figure 1:
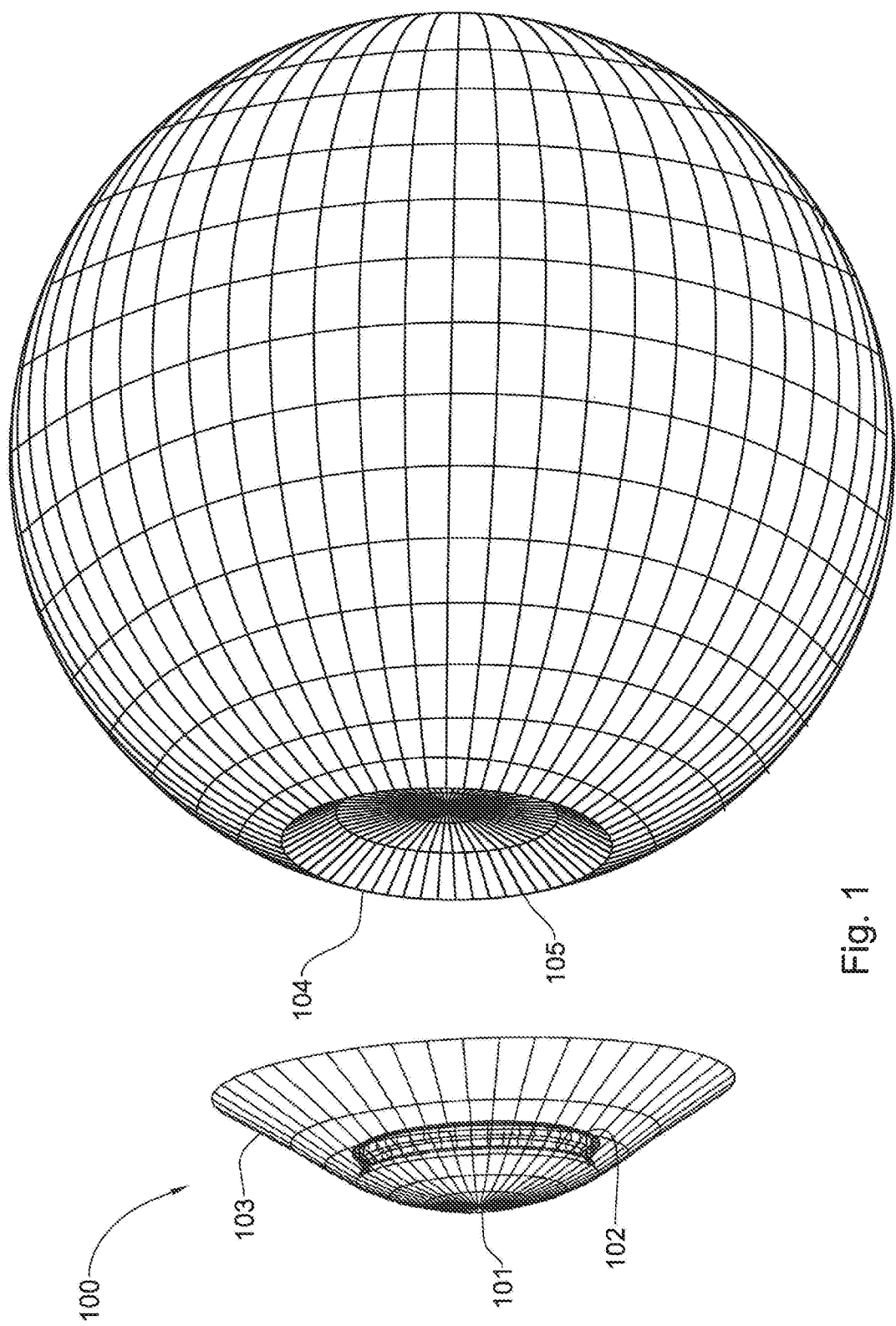
FIG. 1 provides a schematic view of an exemplary keratoprosthesis of the invention and an eye to be implanted.

FIG. 1 shows an embodiment of a keratoprosthesis of the invention 100, consisting of a transparent central optical core 101 and a peripheral skirt 103. The central optical core 101 is extended towards the anterior chamber of the eye with an extension 102 suitable for anchoring said central core in place into the trephined space 104 of the central cornea 105.

Figure 2:
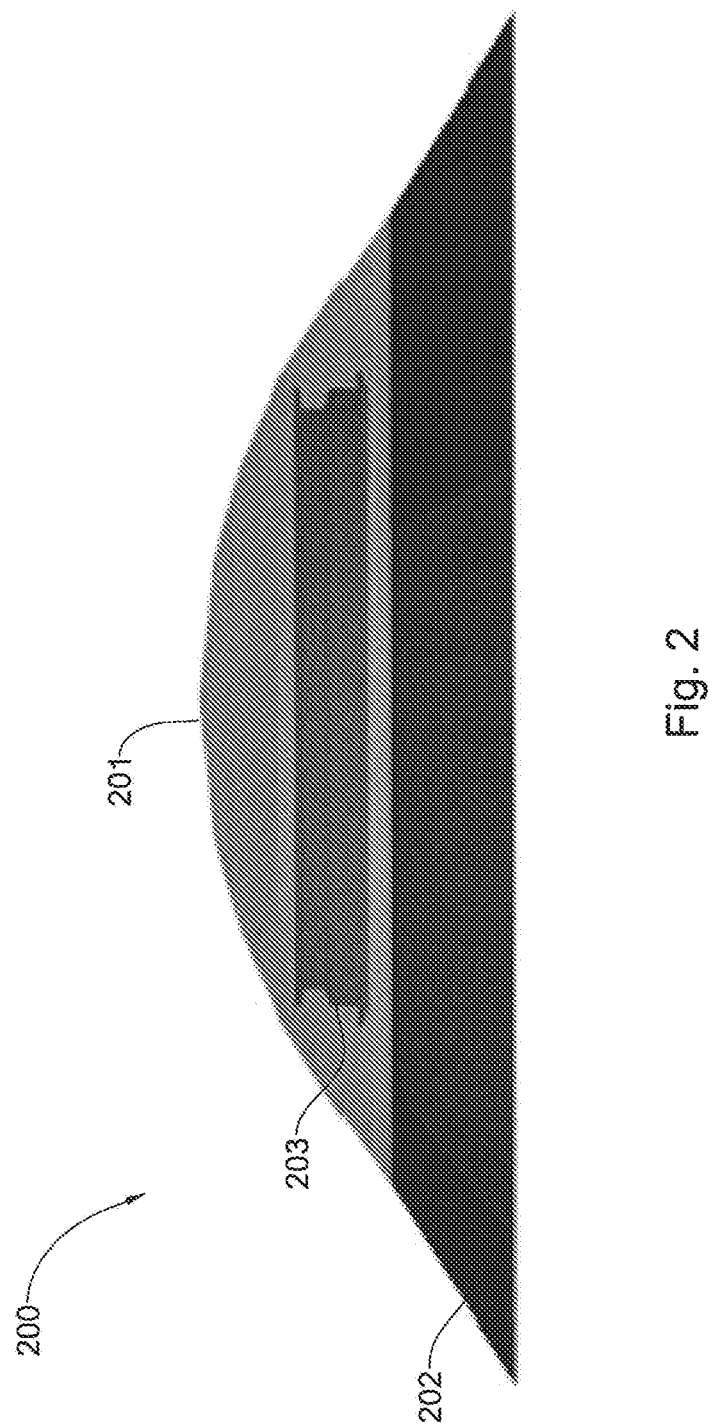
FIG. 2 provides a schematic view of an exemplary keratoprosthesis of the invention.

FIG. 2 shows an embodiment of a keratoprosthesis of the invention 200, consisting of a transparent central optical core 201 and a peripheral skirt 202. The central optical core 201 is extended towards the anterior chamber of the eye with an extension 203 suitable for anchoring said central core in place into the trephined space of the central cornea.

Figure 3:
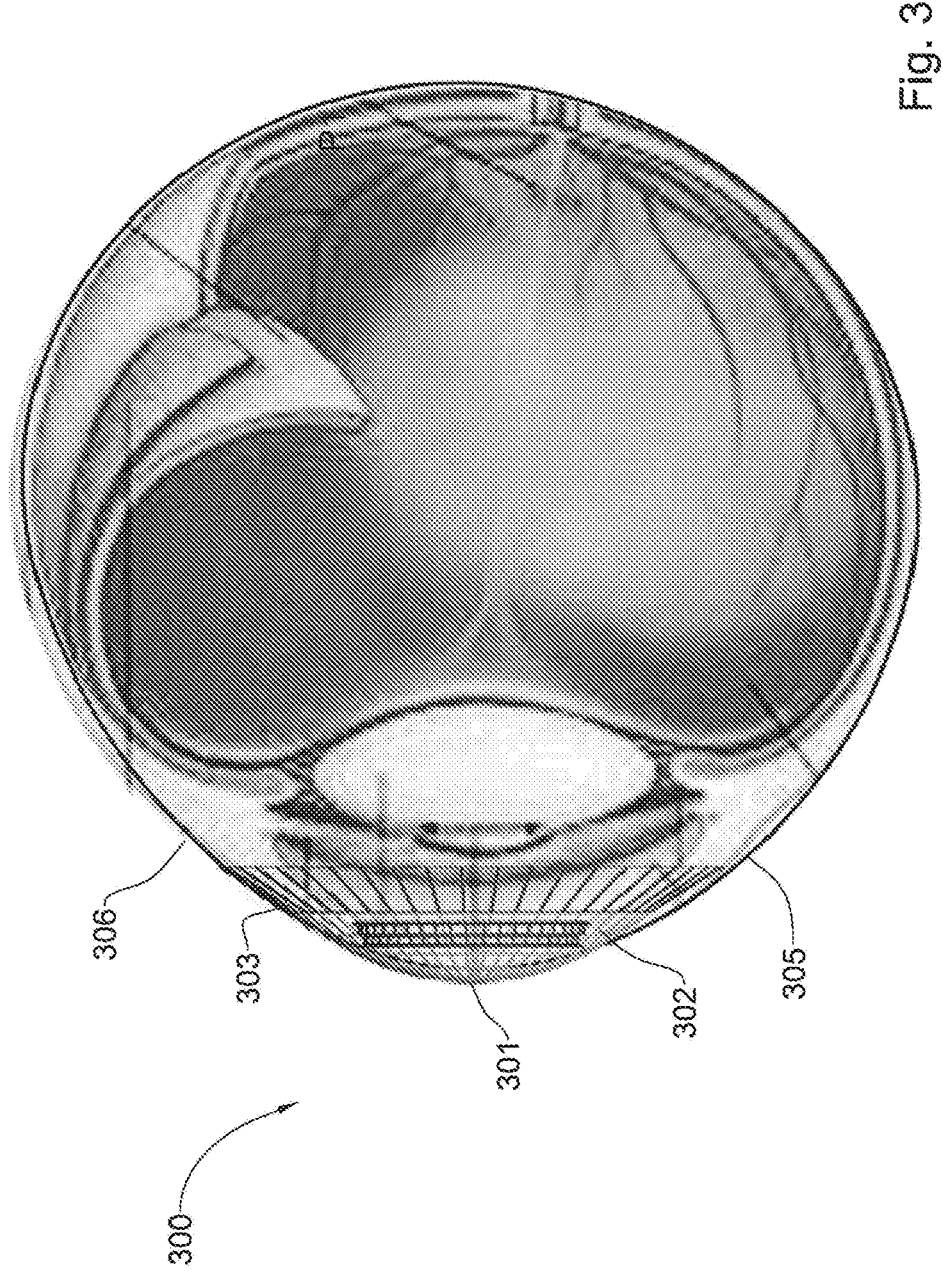
FIG. 3 is a cross section view of an exemplary keratoprosthesis of the invention implanted into the eye.

FIG. 3 shows an embodiment of a keratoprosthesis of the invention 300, placed on the eye of a subject wherein said keratoprosthesis consisting of a transparent central optical core 301 and a peripheral skirt 303. The central optical core 301 is extended towards the anterior chamber of the eye with an extension 302 suitable for anchoring said central core in place into the trephined space 304 (not shown) of the central cornea 305. It is noted that the peripheral skirt 303 when placed on the eye after trephination of the catral cornea extends anteriorly towards the spiral of tillux 306.

Figure 4A:
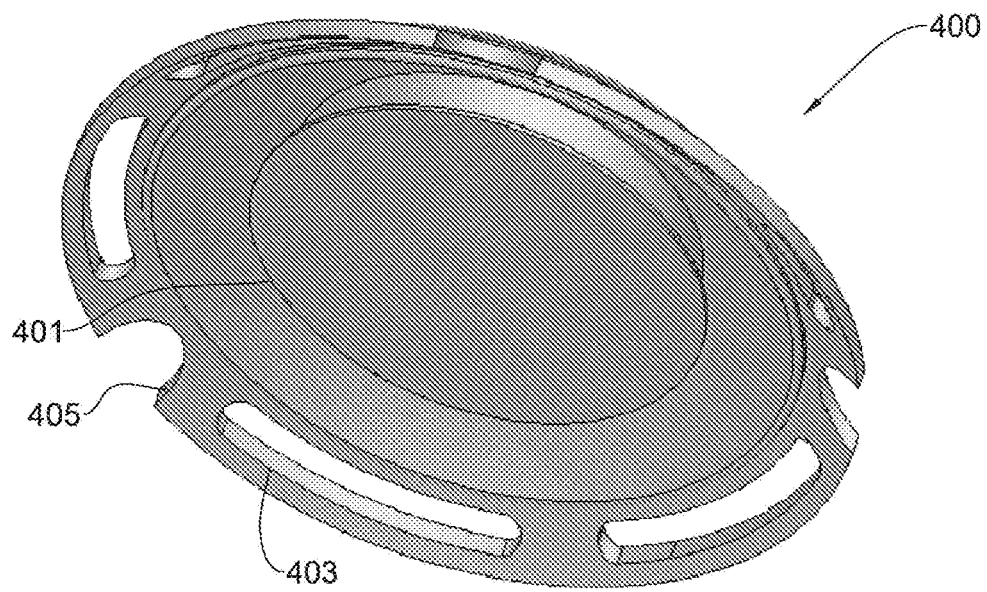
FIGS. 4A-4B is a cross section view of an exemplary keratoprosthesis of the invention.
Figure 4B:
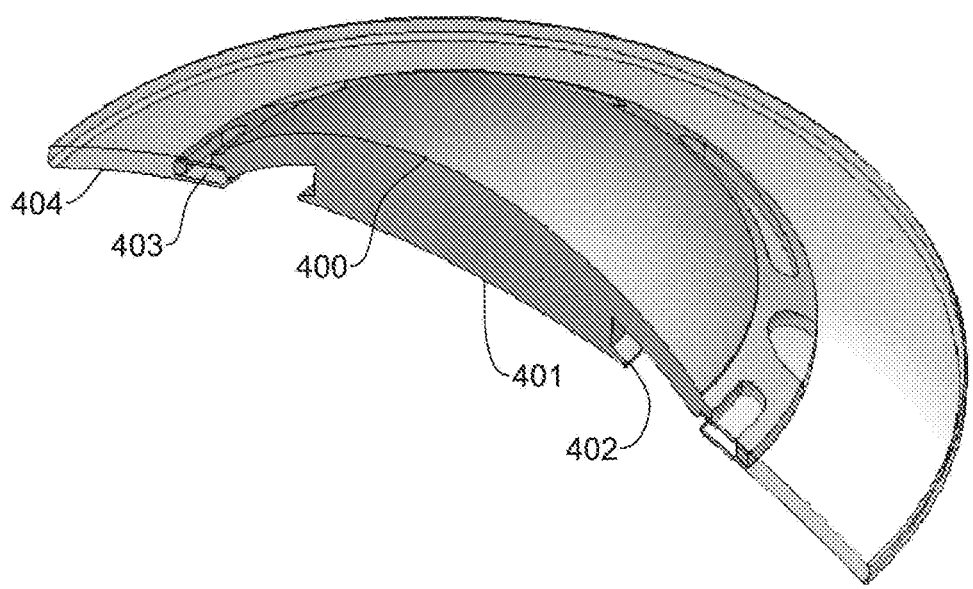

FIGS. 4A-4B is a cross section view of an exemplary keratoprosthesis of the invention. FIG. 4A shows an exemplary central optical core part 400 of the keratoprosthesis. The central optical core 400 is formed of PMMA (approved material for eye implants, similar to the material using in contact lenses) providing a large diameter optical zone. The central core is extended from the concave plane of the central core 401 to form at least one groove 402 shown in FIG. 4B (of multiple optional shapes supporting laser and manual trephination) which enables the implant of the invention to snap and fit into a hole cut in the existing cornea for immediate water-tightness. The at least one groove 402 holds the remaining cornea margins (see also in FIG. 5). The at least one groove 402 also enables thorough clinical exam and inter-ocular access. The central optical core further optionally comprises at least one hole/hollow arches 403 and 405 ensuring optical core-to-skirt (PMMA-to-nanofiber) stability and retention once implanted into human tissue.

Figure 5:
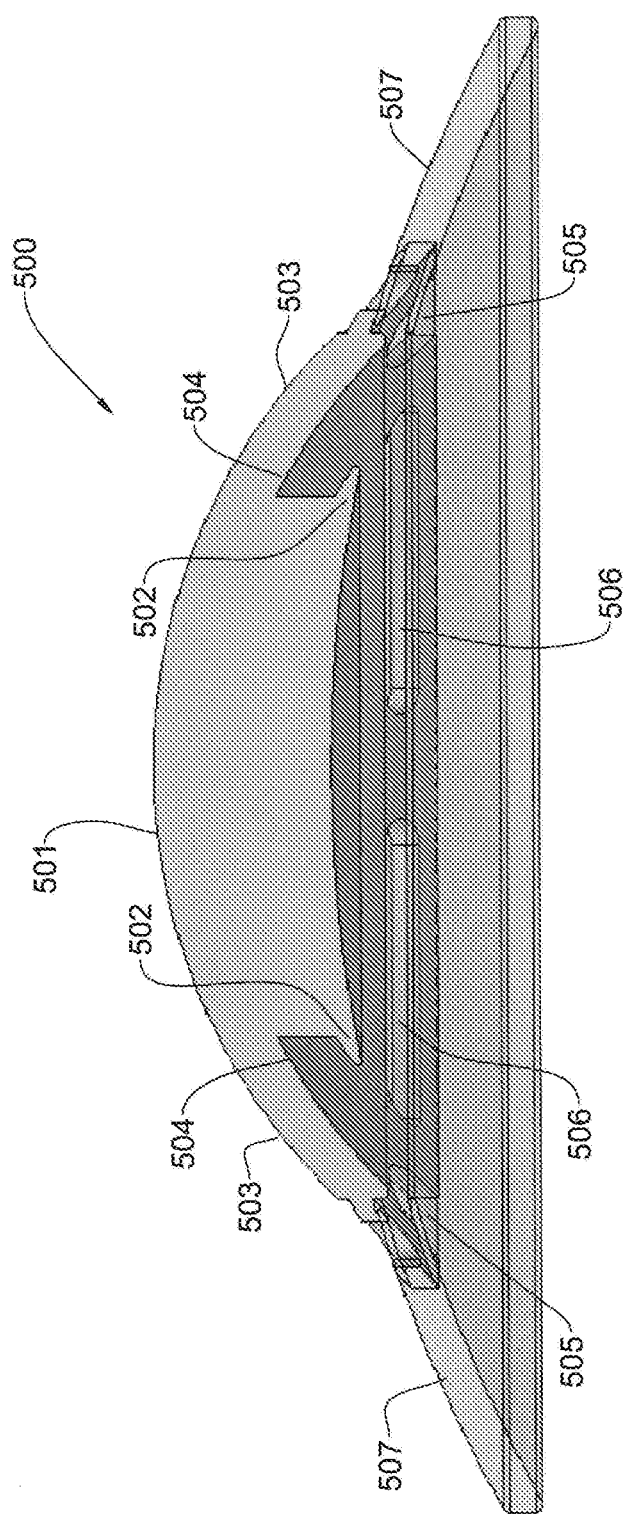
FIG. 5 is a cross section view of an exemplary keratoprosthesis of the invention.

FIG. 4B shows an exemplary central optical core (400) with the peripheral skirt (404). The skirt is positioned subconjunctively and integrates with the conjunctiva, including through at least one hole and arcs 403 cut into the optical element. The skirt is made from electrospun polymer which is biocompatible and stimulates cell growth. The biocompatible porous fibrous material of the Scaffold for cellular proliferation enabling biointegration FIG. 5 is a cross section view of an exemplary keratoprosthesis of the invention 500 implanted into cornea after removal of the diseased cornea. The optical central core 501 is placed above anterial chamber (not shown) and is held tightly into position due to two structural elements including an extension of the optical core 502 and an extension of the exterior optical core 503 forming a groove 504 that holds the remaining margins of the lessered cornea. This at least one groove provides stable positioning of the artificial cornea snapped in and fitting into a hole cut in the existing cornea for immediate water-tightness. The central core also comprises at least one hole and/or hollow arches 505 and 506 ensuring core (501) to skirt (507) (PMMA-to-nanofiber) strength and retention once infiltrated with human tissue. 507 is a representative position of the peripheral skirt of the keratoprosthesis of the invention which is formed of nanofiber electrospun layer enabling cell tissue to grow and assimilate device into the conjunctiva.

Figure 6A:
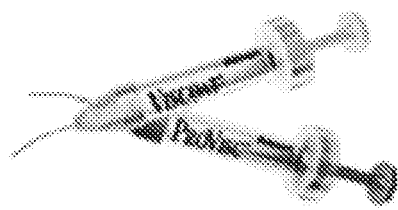
FIGS. 6A-6G provides the steps for the keratoprosthesis procedure using an artificial cornea on the invention showing a single stage, 30 minute procedure that is significantly simpler than any existing solution.

FIGS. 6A-6G provides the steps for the keratoprosthesis procedure using an artificial cornea on the invention showing a single stage, 30 minute procedure that is significantly simpler than any existing solution. The process is performed for example using the following steps:

FIG. 6A the eye is filled with viscoelastic material

Figure 6B:
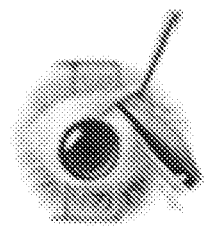

FIG. 6B a peritomy of 360 degrees is made elevating both conjuctive and tenon

Figure 6C:
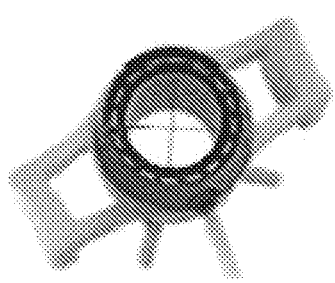

FIG. 6C trephination of the central cornea is carried out

Figure 6D:
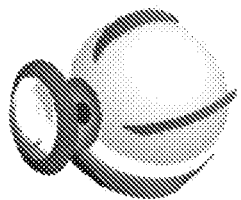

FIG. 6D the optical zone is inserted into the tephinated space

Figure 6E:
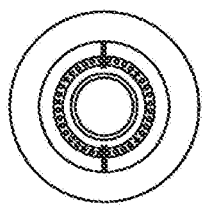
Figure 6F:
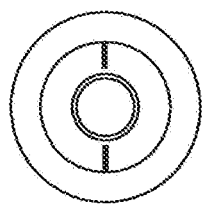
Figure 6G:
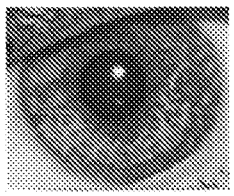

FIG. 6E the biointegrating skirt is laid on the bare sclera and optionally sutured to it FIG. 6F the tenon and conjunctiva is put back in place over the prous skirt and optionally sutured tight FIG. 6G viscoelastic is replaced with BSS (balanced saline solution)

The invention claimed is:

1. A procedure for implanting a keratoprosthesis in a patient in need thereof, the procedure comprising the steps of:
Providing a keratoprosthesis, wherein said keratoprosthesis comprises:
(a) a transparent central optical core;
(b) an annular peripheral skirt attached to and substantially surrounding a perimeter of said central optical core, said annular peripheral skirt comprising an anterior conjunctiva-contacting surface configured to contact a posterior surface of the conjunctiva of a patient's eye, a posterior sclera-contacting surface configured to contact an anterior surface of the sclera of the patient's eye; and
(c) an extended portion extending axially below a surface formed by the central optical core and annular peripheral skirt, said extended portion sized and configured for anchoring said central optical core in place into a trephined space of a central cornea of a patient's eye;

Performing a 360 degree peritomy in the eye of said patient;

Elevating and dissecting both tenon capsule and conjunctiva from sclera of the eye of said patient;

Performing trephination of central cornea of said patient's eye;

Placing the transparent central optical core of said keratoprosthesis into the trephined space of said patient's central cornea;

Placing the peripheral skirt of said keratoprosthesis under the dissected tenon capsule and conjunctiva of said patient's eye;

Replacing tenon capsule and conjunctiva onto the annular peripheral skirt of the keratoprosthesis;

wherein said annular peripheral skirt comprises at least one porous biocompatible layer having pore size of at least 2 μm; and wherein said central optical core has a diameter of at least 3 mm; and wherein said annular peripheral skirt has a width of at least 3 mm and a thickness ranging from about 100 microns to about 2000 microns, wherein the annular peripheral skirt is sized and configured so that it can be placed under the conjunctiva and above sclera of the eye, wherein the width of the annular peripheral skirt extends from attachment to perimeter of central optical core to an outer edge of the annular peripheral skirt.

2. A procedure according to claim 1, wherein said at least one porous biocompatible layer is a polymeric layer.

3. A procedure according to claim 1, wherein said at least one porous biocompatible layer is a nonwoven fabric.

4. A procedure according to claim 1, wherein said at least one porous biocompatible layer comprises nanofibers.

5. A procedure according to claim 1, wherein said at least one porous biocompatible layer is formed by electrospinning process.

6. A procedure according to claim 1, wherein the peripheral skirt further comprises a biomolecule or an antibiotic agent.

* * * * *